US010185773B2

(12) United States Patent
Litoiu et al.

(10) Patent No.: US 10,185,773 B2
(45) Date of Patent: *Jan. 22, 2019

(54) SYSTEMS AND METHODS OF PRECISION SHARING OF BIG DATA

(71) Applicants: Marin Litoiu, Toronto (CA); Mark Shtern, Toronto (CA); Bradley Simmons, Ontario (CA); Michael Smit, Upper Tantallon (CA)

(72) Inventors: Marin Litoiu, Toronto (CA); Mark Shtern, Toronto (CA); Bradley Simmons, Ontario (CA); Michael Smit, Upper Tantallon (CA)

(73) Assignee: Bitnobi, Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/415,713

(22) Filed: Jan. 25, 2017

(65) Prior Publication Data

US 2017/0132326 A1     May 11, 2017

Related U.S. Application Data

(63) Continuation of application No. 14/312,300, filed on Jun. 23, 2014, now Pat. No. 9,590,992.

(60) Provisional application No. 61/976,206, filed on Apr. 7, 2014.

(51) Int. Cl.
    *G06F 17/30*     (2006.01)
    *H04L 29/06*     (2006.01)
    *G06F 21/62*     (2013.01)
    *G16H 10/60*     (2018.01)
    (Continued)

(52) U.S. Cl.
    CPC .. *G06F 17/30867* (2013.01); *G06F 17/30893* (2013.01); *G06F 17/30991* (2013.01); *G06F 21/6245* (2013.01); *H04L 63/10* (2013.01); *G06F 17/30864* (2013.01);
(Continued)

(58) Field of Classification Search
CPC ......... G06F 17/30867; G06F 17/30893; G06F 21/6245; G06F 19/322; G06C 30/0601; G06Q 40/04; G06Q 30/0601
See application file for complete search history.

(56) References Cited

U.S. PATENT DOCUMENTS 6,571,282 B1    5/2003    Bowman-Amuah
8,046,383 B2    10/2011    Weber et al.
8,627,336 B2    1/2014    Wee et al.
(Continued)

OTHER PUBLICATIONS

CA Examination Report (CA2855136) dated Oct. 19, 2016.

*Primary Examiner* — Techane Gergiso
(74) *Attorney, Agent, or Firm* — Chumak & Company LLP

(57) ABSTRACT

An ecosystem that allows fine-grained multi-party control over access to information stored in one or more data sources of a data provider. A requesting party can submit a query job to the data provider. Resellers in the chain can introduce their own query modifiers to the query job, adding additional data access, data transformation and segmentation functions to the query job. The data provider can append its own query modifier to the query job and execute the query job with all of the query modifiers. Access control for each link in the chain is checked before the query modifier for the link is executed. After execution of all query modifiers and the query job, the results can be provided to the requesting party.

14 Claims, 5 Drawing Sheets

(51) Int. Cl.
*G06Q 30/06* (2012.01)
*G06Q 40/04* (2012.01)

(52) U.S. Cl.
CPC ......... *G06Q 30/0601* (2013.01); *G06Q 40/04* (2013.01); *G16H 10/60* (2018.01)

(56) References Cited

U.S. PATENT DOCUMENTS

| | | | | |
|---|---|---|---|---|
| 8,788,476 B2* | 7/2014 | Jones | ................ | G06F 17/30516 707/706 |
| 9,210,178 B1* | 12/2015 | Roth | ................ | H04L 63/105 |
| 9,418,085 B1* | 8/2016 | Shih | ................ | G06F 17/30292 |
| 2003/0126136 A1 | 7/2003 | Omoigui | | |
| 2004/0088174 A1 | 5/2004 | Agrawal et al. | | |
| 2005/0086579 A1* | 4/2005 | Leitner | ................ | G06Q 30/02 715/229 |
| 2006/0235831 A1* | 10/2006 | Adinolfi | ................ | G06Q 40/00 |
| 2007/0214129 A1* | 9/2007 | Ture | ................ | G06F 17/30864 |
| 2008/0289023 A1* | 11/2008 | Wardrop | ................ | G06F 17/30206 726/9 |
| 2009/0083241 A1* | 3/2009 | Jones | ................ | G06F 17/30899 |
| 2009/0089866 A1* | 4/2009 | Yato | ................ | G06F 21/6218 726/6 |
| 2009/0122887 A1 | 4/2009 | Li et al. | | |
| 2009/0254971 A1 | 10/2009 | Herz et al. | | |
| 2011/0213655 A1* | 9/2011 | Henkin | ................ | G06Q 30/00 705/14.49 |
| 2011/0213802 A1* | 9/2011 | Singh | ................ | G06F 17/30539 707/774 |
| 2011/0302226 A1* | 12/2011 | Abadi | ................ | G06F 17/30569 707/825 |
| 2011/0302583 A1* | 12/2011 | Abadi | ................ | G06F 17/30545 718/102 |
| 2012/0310916 A1* | 12/2012 | Abadi | ................ | G06F 17/30445 707/713 |
| 2013/0097593 A1 | 4/2013 | Ravi et al. | | |
| 2013/0124467 A1* | 5/2013 | Naidu | ................ | G06F 17/30575 707/610 |
| 2013/0138626 A1* | 5/2013 | Delafranier | ....... | G06F 17/30442 707/713 |
| 2013/0332931 A1* | 12/2013 | Malewicz | ................ | G06F 7/38 718/102 |
| 2014/0039912 A1* | 2/2014 | Turinas | ................ | G06F 19/322 705/2 |
| 2014/0047422 A1 | 2/2014 | Ravi et al. | | |
| 2014/0059094 A1* | 2/2014 | Shankar | ............ | G06F 17/30091 707/827 |
| 2014/0114994 A1* | 4/2014 | Lindblad | ........... | G06F 17/30545 707/756 |
| 2014/0196115 A1* | 7/2014 | Pelykh | ................ | H04L 63/08 726/4 |
| 2014/0351233 A1* | 11/2014 | Crupi | ................ | G06F 17/30516 707/706 |
| 2015/0199523 A1* | 7/2015 | Hamilton | ................ | G06F 21/60 726/27 |
| 2015/0220080 A1* | 8/2015 | Nixon | ................ | G05B 19/418 700/19 |
| 2016/0224630 A1* | 8/2016 | Cohen | ................ | G06F 17/30463 |

\* cited by examiner

SYSTEMS AND METHODS OF PRECISION SHARING OF BIG DATA

This application is a continuation of U.S. non-provisional application Ser. No. 14/312,300, filed Jun. 23, 2014 and claims priority to U.S. provisional application No. 61/976,206, filed Apr. 7, 2014. U.S. provisional application 61/976,206 and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is data sharing and access control.

BACKGROUND

The following description includes information that may be useful in understanding the present invention. It is not an admission that any of the information provided herein is prior art or relevant to the presently claimed invention, or that any publication specifically or implicitly referenced is prior art.

We are living through the most rapid acceleration of data generation in history: 90% of the world's data has only come into existence since 2010. Buried within the vast and ever-expanding store of data is valuable information. This value cuts across disparate domains including: the biological and life sciences, where cures for disease are being unraveled from the immense quantities of gathered genomic data; the physical sciences, where our understanding of reality is being pieced together at research centers worldwide (e.g., CERN); and the business domain, where social networking, ecommerce and internet search providers seek to monetize every byte of user data to which they gain access.

The more people who have access to this data, the more thoroughly it can be explored and hence the more value can be derived from it; accessibility is one of five key attributes of data. While this is apparent to many Internet companies (e.g., Yahoo has made their indices available to the public through Yahoo! Boss2) it is only beginning to permeate into the general public's consciousness. For example, the City of Toronto has made much of the data it collects available online.

As the amount of data created and stored by organizations continues to increase, attention is turning to extracting knowledge from that raw data, including making some data available outside of the organization to enable data analytics. A common scenario involves retail industry making data available to its suppliers. The adoption of technologies such as the "MapReduce" paradigm has made processing Big Data more accessible, but is still limited to the data that is currently available, often only within an organization. Additionally, existing technologies fail to provide fine-grained control over what information is shared outside an organization.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Thus, there is still a need for a system that allows for fine-grained access control to big data, which can be effectively and efficiently controlled by multiple parties along a distribution chain, and which allows for the parties to transform or otherwise manipulate the data as desired.

SUMMARY OF THE INVENTION

The inventive subject matter provides apparatus, systems and methods in which access to data from data sources can be controlled, and the data itself segmented and transformed according to the requirements of one or more parties.

The inventive subject matter provides an approach to facilitate data sharing that builds upon existing technologies in four main areas: the protection of private or confidential information, the segmentation of a large data set based on various dimensions of the data, the ability to abstract the format of the data shared from the underlying data representations, and a multi-participant process referred to as "chaining". This approach implements a form of data sharing (i.e., need-to-share) in which the data provider is not required to have knowledge about who the data consumer will be.

The systems and methods of the inventive subject matter enable a database query job to be submitted by an analyst or other requesting end user to a data provider (e.g., the entity responsible for accepting and running the query job on a database), such that the database query job can be modified by intermediary parties (e.g., resellers) and the data provider via query modifiers added to the query job that serve to modify the query and, ultimately, the query response returned to the requesting end user.

Upon receiving the modified query job (including all of the added query modifiers associated with each intermediary party), the provider can add its own query modifier to the modified query job and execute the job. The provider executes its own query modifier first, then each additional query modifier in the inverse order from which they were appended to the query job. Thus, the query modifier corresponding to the reseller "closest" to the data provider in the chain of resellers is executed first, then the next closest, and so on. The requesting user's query job is executed last, after the query modifiers of the data provider and all intermediary resellers have been executed. Once the modified query job has been executed, access to the results of the modified query job can be provided to the requesting user.

Each participant in the ecosystem may determine what data they are willing to share with various types of clients (e.g., "downstream" participants in the environment, such as downstream resellers and/or the end user). In embodiments, the participant deciding what to share can be the data provider. In embodiments, the participants can also include resellers between the data provider and the end user. Clients can be differentiated according to various attributes that they possess. Thus, when executing the modified query job, the data provider checks the provided attributes to determine whether each downstream client is authorized to access the requested data prior to running that particular client's query modifier.

The systems and methods of the inventive subject matter can be implemented as a marketplace for Big Data sharing on the cloud. The ecosystem of the inventive subject matter enables and facilitates an enhanced data-as-a-service ("eDaaS"). In an eDaaS, a provider can offer data, and the consumer can consume this data by providing code that runs on a provided infrastructure that is local to the data. This provides the consumer with seamless, online access to data they would not otherwise have access to, without requiring the provider to produce stale copies of data and send them over networks not yet ready for Big Data scale data transport.

The data offerings are advertised within the marketplace. Each defined data offering is generated at runtime by the provider running its internal query modifier on the Big Data collection, passing the results transparently as inputs to a customer's query job (e.g., subsequent query modifiers in the chain and/or, ultimately, the requester's query job). This allows enforcement of the provider's access control policy without additional storage requirements, but also allows the sale and distribution of segments of the data; for example, providing access to data from certain years, certain sources, or certain users without actually creating copies of the data. Thus, the data is decoupled from the view that is provided to the client. This affords the provider complete freedom with regard to how and what data is stored and/or presented (i.e., dynamic constraints can be applied "on the fly").

The inventive subject matter can provide control regarding access, segmentation, and transformation/abstraction to a data provider as well as to intermediary resellers.

As per access control, some of the data provider information may be appropriate to share with most users, other information may be shared only with one type of user, and the remaining information may never be appropriate to share. For example, Twitter might be willing to provide access to analyze Tweets, but only public ones, and might include some user data with each Tweet, but not physical, email, or IP addresses. This decision could be made a priori. Twitter might allow access to more information if the data analyst (via a user interface) provides valid credentials giving them access to some private Tweets, a decision that could be made at run-time.

As per segmentation, not all users need or even desire access to all of the provider available information, and it is possible that not all users could afford access to a complete data set. The data provider can provide useful and marketable subsets of the data. For example, Twitter might provide a segment including only Tweets from Europe or only Tweets from a given month. A provider sharing stock trade data with millisecond accuracy might provide segments per exchange, or per market sector, or per year. This would provide access to Big Data at affordable rates to data analysts unable to afford the complete dataset, or the infrastructure to store/process even a segment of the dataset. These segments could be defined a priori. A segment could be defined at run-time to support custom segments, or to allow pay-as-you go (i.e. access is allowed only until pre-purchased credits are consumed).

As per transformation/abstraction, the provider may wish to share only a transformed version of their data—perhaps de-identified for privacy reasons, or changed to a different data structure. For example, a data provider may not wish to reveal a proprietary compact binary representation of data, and provide instead a JSON-encoded string. Transformations are defined a priori, but can be applied selectively at run-time—for example, searching text strings for patterns that resemble phone numbers and obscuring the numbers.

In an illustrative embodiment, the systems and methods are implemented via the Hadoop framework using the MapReduce technology. In this embodiment, the query modifier is known as a "Modifying Map" that added to an end user's submitted MapReduce job.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
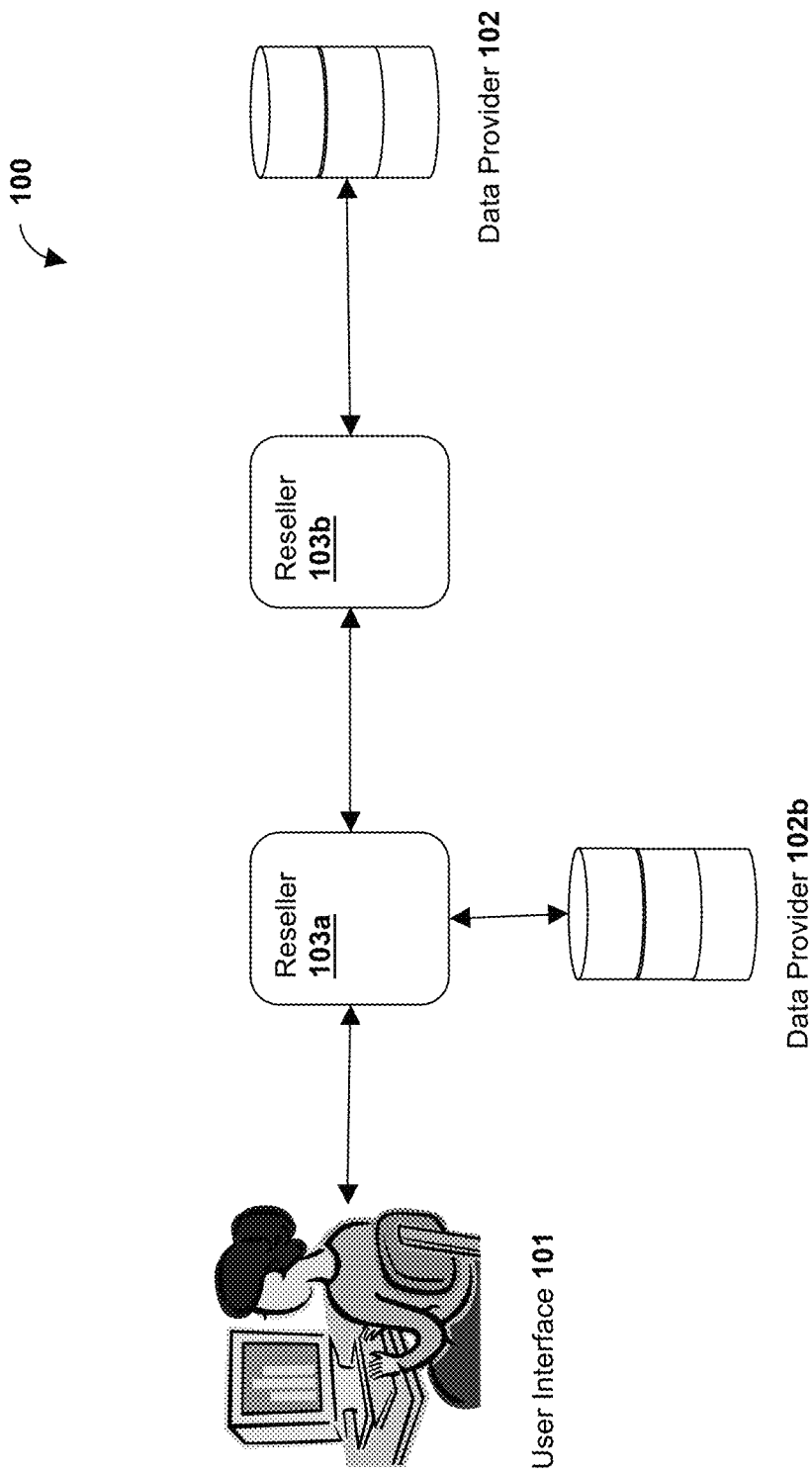
FIG. 1 provides an overview of the multi-reseller data access chain environment, according to embodiments of the inventive subject matter.

Throughout the following discussion, numerous references will be made regarding servers, services, interfaces, engines, modules, clients, peers, portals, platforms, or other systems formed from computing devices. It should be appreciated that the use of such terms is deemed to represent one or more computing devices having at least one processor (e.g., ASIC, FPGA, DSP, x86, ARM, ColdFire, GPU, multi-core processors, etc.) configured to execute software instructions stored on a computer readable tangible, non-transitory medium (e.g., hard drive, solid state drive, RAM, flash, ROM, etc.). For example, a server can include one or more computers operating as a web server, database server, or other type of computer server in a manner to fulfill described roles, responsibilities, or functions. One should further appreciate the disclosed computer-based algorithms, processes, methods, or other types of instruction sets can be embodied as a computer program product comprising a non-transitory, tangible computer readable media storing the instructions that cause a processor to execute the disclosed steps. The various servers, systems, databases, or interfaces can exchange data using standardized protocols or algorithms, possibly based on HTTP, HTTPS, AES, public-private key exchanges, web service APIs, known financial query protocols, or other electronic information exchanging methods. Data exchanges can be conducted over a packet-switched network, the Internet, LAN, WAN, VPN, or other type of packet switched network.

One should appreciate that the systems and methods of the inventive subject matter provide various technical effects, including providing data access and analysis functions without requiring copying or transmitting large data sources for use by a client.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

The inventive subject matter allows data analysts to run database query jobs on some portion of a data provider's Big Data, while affording the data provider total, fine-grained control over access to each piece of data, and allowing run-time transformation of the data. This run-time mediation is provided by prefixing the user's query job with an additional query modifier (thus creating a modified query job), where the provider can implement access control, data segmentation, and/or data transformation. The run-time transformation of the query serves to modify or restrict access to data before the consumer or end-user can access it. The query modifier can also control database query tasks at a low-level, including measuring or limiting execution time.

Aspects of the inventive subject matter as applied to MapReduce technology are described in the inventors' papers "Toward an Ecosystem for Precision Sharing of Segmented Big Data" and "Enabling an Enhanced Data-as-a-Service Ecosystem", both of which are incorporated by reference herein in their entirety.

The term "Big Data" is generally used to describe collections of data of a relatively large size and complexity, such that the data becomes difficult to analyze and process within a reasonable time, given computational capacity (e.g., available database management tools and processing power). Thus, the term "Big Data" can refer to data collections measured in gigabytes, terabytes, petabytes, exabytes, or larger, depending on the processing entity's ability to handle the data. As used herein, and unless the context dictates otherwise, the term "Big Data" is intended to refer to collections of data stored in one or more storage locations, and can include collections of data of any size. Thus, unless the context dictates otherwise, the use of the term "Big Data" herein is not intended to limit the applicability of the inventive subject matter to a particular data size range, data size minimum, data size maximum, or particular amount of data complexity.

The inventive subject matter can be implemented on any suitable database or other data collection management technology. For example, the inventive subject matter can be implemented on platforms such as Hadoop-based technologies generally, MapReduce, HBase, Pig, Hive, Storm, Spark etc.

FIG. 1 provides an overview of exemplary ecosystem 100 of the inventive subject matter. As shown in FIG. 1, the ecosystem 100 includes a user interface 101 (e.g., through which a user or a data analyst access the system), and a data provider 102. In embodiments, the ecosystem 100 can also include one or more resellers 103 between the user 101 and the data provider 102. In the illustrative example of FIG. 1, the ecosystem 100 shows two resellers 103a,103b. However, it is contemplated that any number of resellers 103 can be included. In embodiments, the ecosystem 100 can include no resellers, with the user interface 101 communicating directly with the data provider 102. A single user interface 101 is illustrated in FIG. 1 for simplicity and ease of understanding, but it is contemplated that the ecosystem 100 supports a plurality of user interfaces 101 that can interact with the ecosystem 100 via one or more of the resellers 103 and/or one or more data providers 102.

In embodiments, the ecosystem 100 can include more than one data provider 102, which can be communicatively connected to any of the resellers 103 and/or to the user interface 101. In the example shown in FIG. 1, data provider 102b is shown as being communicatively connected to reseller 103a. Thus, user interface 101 can access data provided by data provider 102 via resellers 103a and 103b, and can access data from data provider 102b via reseller 103a.

Each of the components the ecosystem 100 (i.e., the user interface 101, the data providers 102, resellers 103, etc.) can be communicatively coupled with each other via one or more data exchange networks (e.g., Internet, cellular, Ethernet, LAN, WAN, VPN, wired, wireless, short-range, long-range, etc.).

The data provider 102 can include one or more computing devices programmed to perform the data provider's functions including receiving query jobs (which can include modified query jobs and non-modified query jobs) from user interface(s) 101 and/or resellers 103, modifying the received query jobs according to the data provider's modifiers, executing the query jobs (including any modifications thereto) and returning the results to the corresponding requesting user interfaces(s) 101. Thus, the data provider 102 can include at least one processor, at least one non-transitory computer-readable storage medium (e.g., RAM, ROM, flash drive, solid-state memory, hard drives, optical media, etc.) storing computer readable instructions that cause the processors to execute functions and processes of the inventive subject matter, and communication interfaces that enable the data provider 102 perform data exchanges with user interface(s) 101 and a reseller(s) 103. The computer-readable instructions that the data provider 102 uses to carry out its functions can be database management system instructions allowing the data provider 102 to access, retrieve, and present requested information to authorized parties, access control functions, etc. The data provider 102 can include input/output interfaces (e.g., keyboard, mouse, touchscreen, displays, sound output devices, microphones, sensors, etc.) that allow an administrator or other authorized user to enter information into and receive output from the data provider 102 devices. Examples of suitable computing devices for use as a data provider 102 can include server computers, desktop computers, laptop computers, tablets, phablets, smartphones, etc.

The data provider 102 can include the databases (e.g. the data collections) being made accessible to the user interface(s) 101 and reseller(s) 103. The data collections can be stored in the at least one non-transitory computer-readable storage medium described above, or in separate non-transitory computer readable media accessible to the data provider 102's processor(s). In embodiments, the data provider 102 can be separate from the data collections themselves (e.g., managed by different managing entities). In these cases, the data provider 102 can store a copy of the data collections which can be updated from the source data collections with sufficient frequency to be considered "current" (e.g. via a periodic schedule, via "push" updates from the source data collections, etc.). Thus, the entity or administrator operating the data provider 102 can be considered to be the entity responsible for accepting and running the query jobs, regardless of actual ownership of the data.

Administrators or other members of data provider 102 can assess their data (e.g., Big Data), and decide which portions of it are to be made accessible to some degree. For example, the determination can be regarding the portions of data to be made available outside an organization, among various business units internal to an organization, etc. The size and scope of the portions can be determined entirely a priori, or can be determined at run-time based on information provided by the user interface 101 (and any intermediary resellers 103). These logical partitions of the physical data are referred to herein as data sources. Establishing restricted subsets of the data for access facilitates data access control, segmentation, and transformation/abstraction for the data provider 102.

To make the data available to users (via user interfaces 101) and resellers 103, the data provider 102 defines its data sources and implements a query modifier to be applied for each data source. The data provider 102 can also provide information about all available data sources (e.g., what data is provided, which "provider interface" the user's query and any reseller's query modifier must implement including: the format and data type of the incoming data, the approximate size of the data, cost definitions, etc.) through a web service API. Users' interaction with the data sources is enabled through this API. In embodiments, the web service can be specified to be standardized across all providers, allowing for easy integration.

The user interface 101 can implement the prescribed "provider interface", and submit their compiled code to the provider's web service along with any required parameters. The data analyst can, via the user interface 101, monitor the status of their job or retrieve the results through the same web service. The user interface 101 can run their own client for communicating with the web service, or use a client offered through a Software-as-a-Service (SaaS) delivery model, where jobs are submitted and monitored through a client-facing user interface with the actual communication handled behind-the-scenes.

The user interface 101 can comprise one or more computing devices that enables a user or data analyst to access data from data provider 102 by creating and submitting query jobs. The user interface 101 can include at least one processor, at least one non-transitory computer-readable storage medium (e.g., RAM, ROM, flash drive, solid-state memory, hard drives, optical media, etc.) storing computer readable instructions that cause the processors to execute functions and processes of the inventive subject matter, and communication interfaces that enable the user interface 101 perform data exchanges with data provider 102 and reseller(s) 103. The user interface 101 also includes input/output interfaces (e.g., keyboard, mouse, touchscreen, displays, sound output devices, microphones, sensors, etc.) that allow the user/data analyst to enter information into and receive output from the system 100 via the user interface 101. Examples of suitable computing devices for use as a user interface 101 can include servers, desktop computers, laptop computers, tablets, phablets, smartphones, "thin" clients, "fat" clients, etc.

Figure 2:
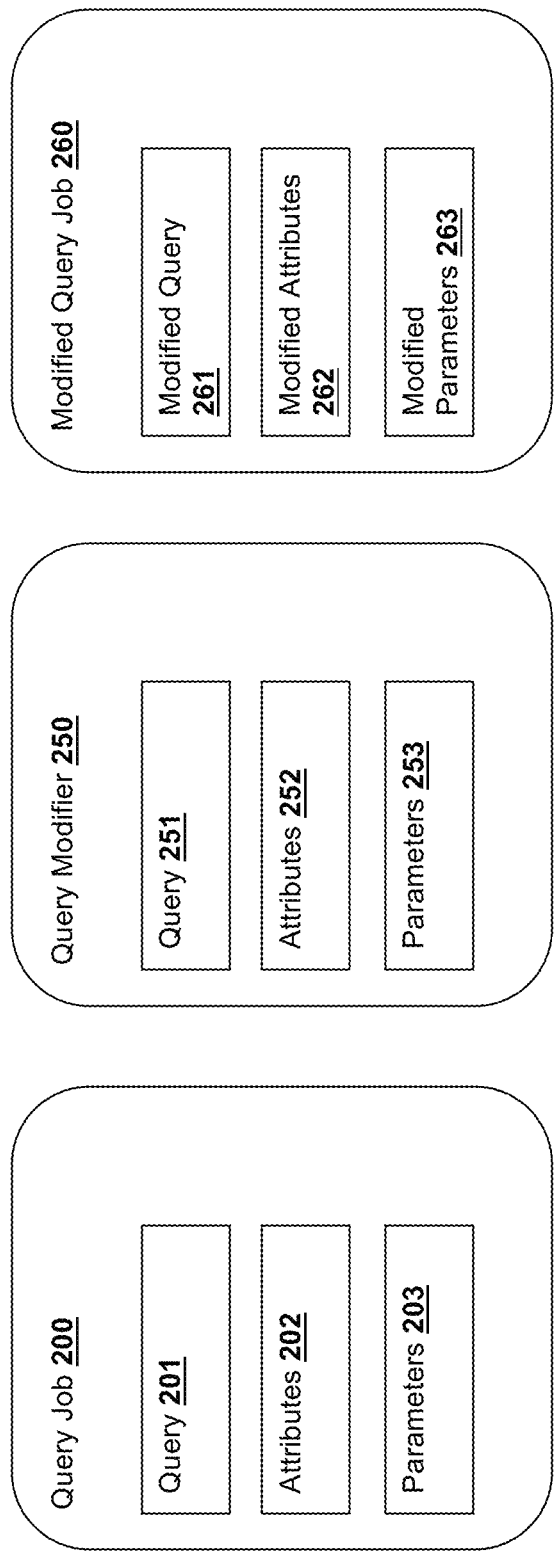
FIG. 2 provides illustrative examples of a query job, a query modifier, and a modified query job, according to embodiments of the inventive subject matter.

To access or obtain data from the data provider 102, the user interface 101 can create a query job and submit it to the data provider 102 (either directly or via a reseller 103, depending on the layout of the ecosystem 100). FIG. 2 provides an illustrative example of a query job 200 generated by the user interface 101, a query modifier 250 generated by a reseller 103 and/or a data provider 102, and a modified query job 260 illustrating a query job 200 modified by appended query modifier 250.

As shown in FIG. 2, a query job 200 can include at least one database query 201 (e.g., the query step(s) to be performed by the data provider 102, such as a database query) to be executed by the data provider 102 to retrieve and provide the user-requested data, user attributes 202 (e.g., information about the requesting user and/or the user interface 101, used as credentials by the data provider 102), and required parameters 203. The database query 201 can include an identification of the data requested (e.g., via a query step) and one or more transformation steps to be performed on the data for presentation to the user via the user interface 101. The user attributes 202 can include attributes such as user identifiers, role identifiers, account information, user age, user social security number, organization identifiers, analysis permissions (e.g., what kind of analysis may be performed by the user on the data), authorization level, etc. Parameters 203 can include data format and data type identifiers (e.g., the formats/types of the query 201, requested data formats/types for a response, etc.), one or more data source identifiers (e.g., the data sources published by the data provider 102 to which the query 201 is to be applied), and any additional runtime conditions (e.g., runtime duration limit of the query before aborting the query, a maximum cost to be incurred according to access time and/or resource usage, etc.)

As discussed above, in embodiments of the inventive subject matter, the basic user-provider interaction is augmented with resellers 103. While some data providers 102 might have the ability to offer extensive segmentation and transformation of data, they may prefer to focus on their core competencies, or only performing some functions and services on the data. Other data providers 102 may not have the ability to provide all of the data services requested. For example, a data provider 102 can elect to (or may only be able to) only provide access control and privacy protection to the data they are sharing. Entities operating resellers 103 may establish relationships with data providers and sell access to the provider's infrastructure, accepting query jobs from user interface(s) 101 and running them on the provider 102. A reseller 103 can offer additional segmentation or transformation to produce value-added data sets, or smaller, more affordable data sets. In an example having data provided by Twitter, one reseller might segment Tweets by estimated household income based on geographic information; another might augment Tweets with a popularity metric; a third might sell subsets of the overall data set where only Tweets mentioning politics or certain products are included. A data analyst could, via user interface 101, choose one of these smaller data sets to reduce costs. For simplicity of illustration, FIG. 1 shows only two resellers 103a,103b chained together. However, resellers 103 can be chained together in (theoretically) unlimited series. For example, a fourth reseller might sell segmented access to the first reseller's Tweet+Income data set, by income tax bracket.

The reseller 103 can comprise one or more computing devices which can include at least one processor, at least one non-transitory computer-readable storage medium (e.g., RAM, ROM, flash drive, solid-state memory, hard drives, optical media, etc.) storing computer readable instructions that cause the processors to execute functions and processes of the inventive subject matter associated with the reseller, and communication interfaces that enable the reseller 103 to perform data exchanges with data provider 102, user interface 101, and other reseller(s) 103. The reseller 103 also includes input/output interfaces (e.g., keyboard, mouse, touchscreen, displays, sound output devices, microphones, sensors, etc.) that allow a reseller administrator or other authorized user to enter information into and receive output from the reseller 103 and other components of the system 100. Examples of suitable computing devices for use as a reseller 103 can include servers, desktop computers, laptop computers, tablets, phablets, smartphones, "thin" or "fat" clients, etc.

A reseller 103 adds value as an intermediary by further segmenting or augmenting data from the provider 102. In embodiments, the reseller may host their own infrastructure, acquire data from multiple providers, and run query jobs directly on their infrastructure where this data is aggregated, filtered, or otherwise combined and transformed. For example, a reseller 103 might offer a data set of users and social trust scores, with data from multiple providers collected into a local data source instance that accepts query jobs from users. In this case they appear to the user interface 101 as the provider, and function as a provider 102 when receiving jobs for their own data sources. When they run jobs to acquire copies of the data from providers 102, they behave like a user interface 101. They may also function as a normal reseller, accepting query jobs for submission to the provider. Managing these multiple roles is the responsibility of the reseller 103; throughout this text, references to providers 102 include these "enhanced resellers" when in their provider role, and likewise for reseller and user interface roles. FIG. 1 provides an illustrative example of the "enhanced reseller" 103a. In this example, reseller 103a can pass query jobs from user interface 101 to data provider 102 (via reseller 103b), to provider 102b directly, or both.

Figure 3:
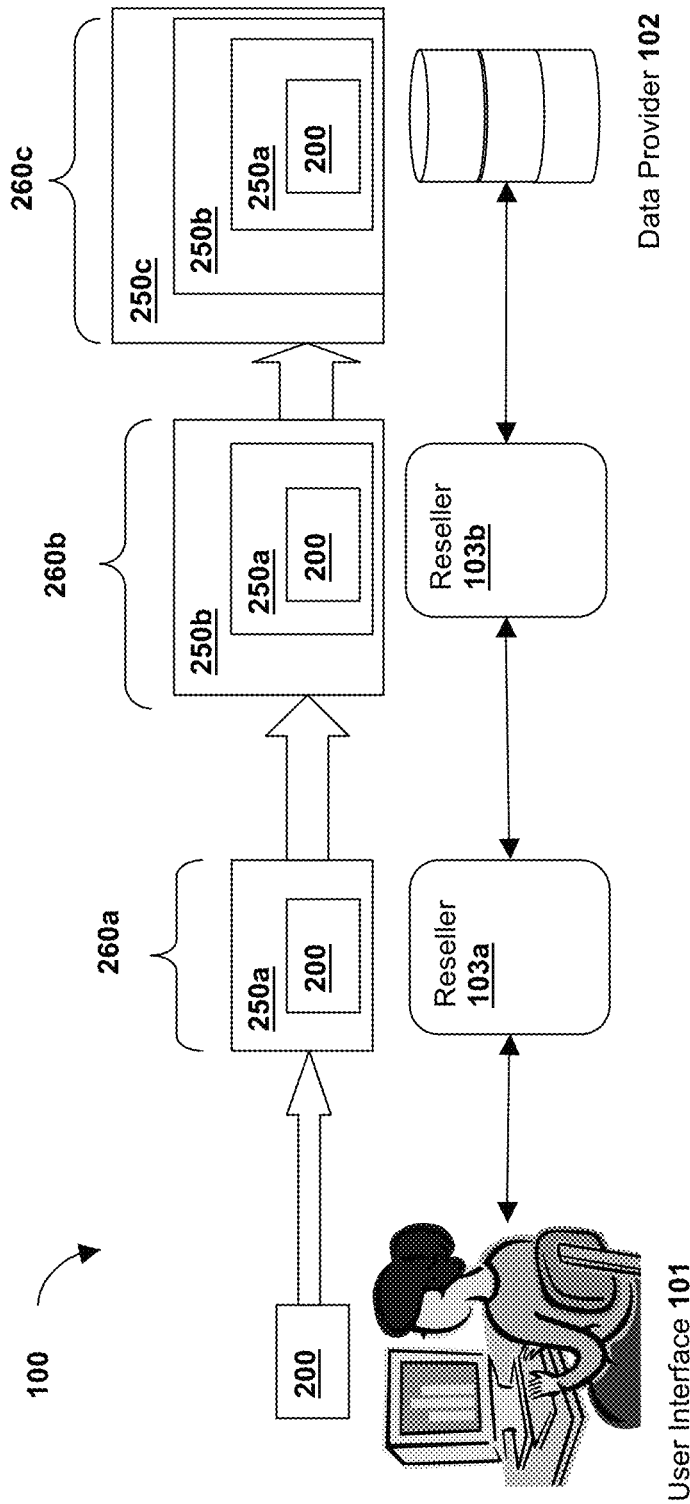
FIG. 3 provides an overview of the addition of query modifiers to a query job in the multi-reseller environment of FIG. 1, according to embodiments of the inventive subject matter.

To achieve added layers of runtime data mediation, reseller(s) 103 and the data provider 102 are programmed to add their own query modifier 250 to a query job 200 in between the user interface 101 and the execution of the job by the data provider 102. In an ecosystem having a chain of resellers and data providers, multiple query modifiers 250 can be appended to the initial query job 200, such that one query modifier 250 can appended "over" the query modifier 250 of the preceding link in the chain. FIG. 3 provides an illustrative overview of the ecosystem 100 whereby query job 200 can be this submitted from the user interface 101 to the data provider 102 via resellers 103a,103b.

For the purposes of simplicity and clarity, references to "upwards", "upstream" or "up the chain" are intended to reference a flow from left to right in FIG. 3 (i.e., in a direction toward the data provider 102 and away from user interface 101). Conversely, the use of "downwards", "downstream" or "down the chain" are intended to refer to a direction from right to left (i.e., in the direction toward the user interface 101 and away from the data provider 102). Additionally, unless context dictates otherwise, a "requestor" or "requester" as used herein is intended to refer generally to an entity within the system (e.g., the user interface 101 or a reseller 103) submitting a request (i.e. query job, modified query job, etc.) to the data provider 102. Generally, the use of "requester" or "requestor" will refer to the requesting entity closest to the data provider (i.e. the requesting entity immediately downstream of the provider 102). The requestor/requester can similarly be referred to as the "first requester", "first requestor", "direct requester", and/or "direct requestor". Subsequent entities downstream can be referred to as second requestor, third requestor, etc., according to their position in the chain relative to the data provider. Thus, in FIG. 3, the reseller 103b can be considered the requester, the reseller 103a the second requester, and the user interface 101 the third requester. The user interface 101 can also be referred to as the "originating requester".

As shown in FIG. 3, the user interface 101 provides the created query job 200 to the first reseller 103a. The first reseller 103a appends its query modifier 250a to the query job 200. The combination can be considered to be a modified query job (in this case modified query job 260a). The first reseller 103a passes the modified query job 260a (again, having the original query job 200 and the query modifier 250a) to the next link in the chain, which in this example is reseller 103b.

As with reseller 103a, reseller 103b similarly appends its own query modifier 250b to the modified query job 260a, which results in modified query job 260b having the query job 200, the query modifier 250a and the query modifier 250b. The reseller 103b passes the modified query job 260b to the data provider 102. The data provider 102 appends its own query modifier 250c to result in modified query job 260c. Modified query job 260c is the query job that will be executed by the data provider 102, the results of which are provided to the user interface 101.

During execution of modified query job 260c, the data provider 102 will execute the queries of the query modifiers 250 and original query job 200 in the reverse order in which they were appended to the query job. Thus, at runtime, the data provider 102 first executes the queries of query modifier 250c, then the queries of query modifier 250b, then those of query modifier 250a, and finally the queries of query job 200. As such, a query modifier appended to a query job (or modified query job) can be considered to "wrap" the query job.

Returning to FIG. 2, the query modifier 250 can include a query 251, attributes 252 and parameters 253.

The query 251 of a query modifier 250 are a reseller 103's database query(s) to be performed by the data provider 102 at run-time prior to the execution of the query 201 generated by the user interface 101. In the case of a query modifier 250 of a data provider, the query 251 can be the database query(s) to be applied to the data source by the data provider 102 prior to the execution of any requesting party's queries.

Query modifier 250 can include restrictions on bandwidth, execution duration, processing power usage (e.g., percentage of available CPU power), restrictions on data usage, restrictions on analysis type (e.g., data associations or correlations, statistical analysis usage, etc.), etc. Other functions can include reporting or value chain management functions that can include reporting to the provider 102 or to resellers 103 along the chain (e.g., metrics of parts of chain consumed the most by users, data sources most often accessed, most often requested but denied, etc.).

For example, in a medical setting, query modifiers 250 can include restriction functions that limit analysis on the otherwise accessible data such that confidentiality for a patient or population of patients is potentially compromised.

The query modifier 250's query 251, attributes 252, and parameters 253 can mirror those of the query job 200. Thus, the query 251 can include the same type of queries as query 201 that are executable by a data provider 102 upon runtime. In embodiments, the queries 251 of a query modifier 250 can include less than the full query of a particular type. For example, suppose that a database query step can include a data filtering step and a data aggregation step whereby, when executed by a database management system, first filters the data according to the query step of the query then aggregated the filter data for presentation to the querying user. The query 201 of the query job 200 would include both the data filtering step and the data aggregation step. However, the query 251 of the query modifier 250 can include only the data filtering step. In another example whereby the inventive subject matter is implemented via MapReduce technology, the query 251 includes a map step that is appended to a map step of query 201. However, where the query 201 includes a reduce step, the query 251 does not include a reduce step. Instead, the reduce step of the query 201 is executed after the map step of query 251 is executed and then the map step of query 201 is executed.

The attributes 252 can mirror those of attributes 202, with the attributes 252 corresponding to the reseller 103 that is applying the query modifier 250 to the query job 200.

The parameters 253 can include parameters mirroring the parameters 203 of the query job 200. Additionally, the parameters 253 of a query modifier 250 include a filter step whereby, prior to executing the next query in the chain, verifies that the next entity in the chain (to whom the next query corresponds) is authorized to access the data (and to perform the queries). Thus, the filter step can include a set of access control rules that can be executed at runtime. The filter step can include a set of access attributes that the next downstream link in the chain must possess in order to access the data. The filter step can also include a set of prohibited queries, associations, and analysis on the data that, if a part of next queries in the chain, cause access to be denied. The filter step of a query modifier 250 can be considered to be the access control rules implemented by the entity generating the particular query modifier 250 for downstream entities.

The output of the execution of query 252 of query modifier 250 generally can be referred to as a modifier output. The output of the execution query 202 of the query job 200 generally can be referred to as a job output, a user output, a job result, or a user result. In line with the description of a "requester" herein, the output of running a requester's query generally can be considered a requester output. It should be noted that the terms modifier output and a requester output can refer to the same data output if the requester is a reseller. Likewise, it is possible that the requester output and the user output (used collectively to represent all ways of referencing the output of the query job 200) can refer to the same data output if the requester is the user interface.

The modified query job 260 of FIG. 2 includes a modified query 261, modified attributes 262, and modified parameters 263. For the purposes of illustration, the modified query job 260 of FIG. 2 is shown as the combination of query job 200 and query modifier 250. However, the modified query job 260 can be a combination of the query job 200 and more than one query modifier 250 (such as the modified query jobs 260b and 260c illustrated in FIG. 3). As shown in FIG. 2, the modified query 261 can be considered to be the query 201 with the appended query 251. The modified attributes 262 can be an aggregated list of attributes 202, 252. However, it is noted that the modified attributes 262 is shown as a single grouping for the purposes of illustration. Thus, the modified attributes 262 maintain an organized separation, organization and correlation to their original attribute sets 202, 252 such that attributes 202 associated with the query job 200 can be associated with the query 201 and attributes 252 associated with the query modifier 250 can be associated with the query 251 (such as for access control, proper identification, etc.). Similarly, the modified parameters 263 can be considered to be the parameters 203, 253 collectively, but organized such that they can each be applied at runtime as needed to execute the querys 201, 251, respectively.

Figure 4:
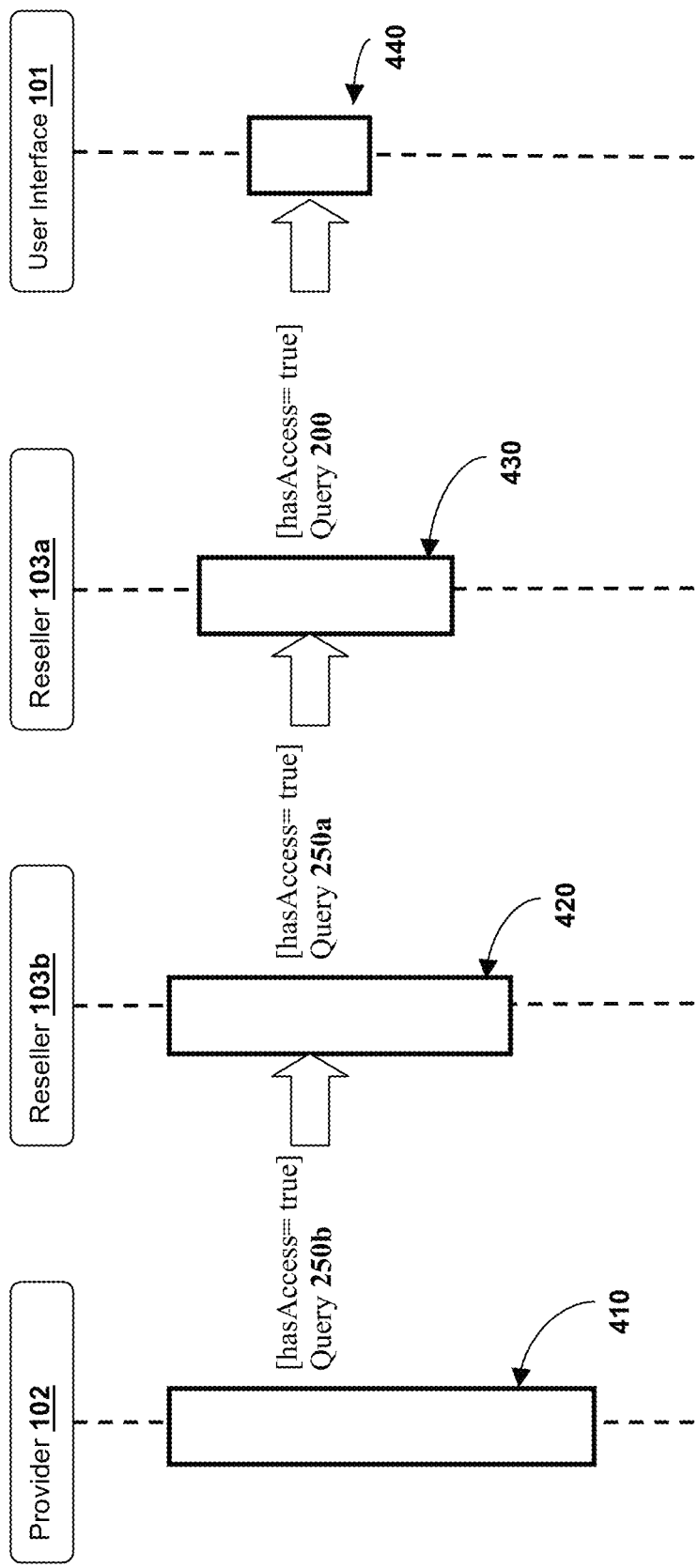
FIG. 4 provides an illustrative example of the functionality of the access control logic controls, according to embodiments of the inventive subject matter.

FIG. 4 provides a diagram illustrating the implementation of the filter steps during the runtime execution of a packaged query job. In this example, the query job being processed is the query job constructed in FIG. 3.

Within the running modified query job, starting from the provider 102, each participant's filter step checks to see if the next participant has access to a given data record before invoking the next participant's query(s).

At runtime, the data provider 102 executes the query of the provider's query modifier 250c on the data source identified by one or more of the resellers 103a,103b and the user interface 101, which results in a modifier output 410 (e.g., a subset of the data source or other output of the query modifier 250c). After executing the query associated modifier 250c, the data provider 102 executes the filter step of the query modifier 250c to verify that the reseller 103b has access to the data of the output 410 (including performing the queries requested by the reseller 103b). As illustrated here, the result is "true", and as such, the query modifier 250b of the reseller 103b is invoked and the queries executed. Similarly, at the end of queries associated with modifier 250b, an output 420 remains and the filter step associated with modifier 250b (implemented by reseller 103b) verifies that reseller 103a has access to the data of output 420. This process continues down the line, until ultimately the user output 440 remains, to be provided to the user interface 101. As shown in FIG. 4, each of the outputs 410,420,430,440 is progressively smaller as each is a subset of the previous output.

The inventive subject matter allows for users having established relationships to a reseller 103 and/or a provider 102 to, via the user interface 101, submit query jobs to a provider 102 (optionally via a reseller 103). This can be sufficient for public data, where the provider 102 only supplies information that they are willing to made public. In embodiments, the inventive subject matter can include Attribute-Based Access Control ("ABAC") which, when combined with the features of the web service offered by each provider/reseller, facilitates a larger ecosystem for sharing public, semi-private, and private data sets with verified users. In the ecosystem of the inventive subject matter, users can discover available data sources and submit jobs to them easily, and providers can authorize users to run query jobs without knowing all of the details about the user or having an established relationship.

In this approach to ABAC, a user can register with a central service (for convenience, we call this the "marketplace"; a distributed, reliable service). They can add attributes to their account by simply adding them (user-signed attributes) or by requesting that a third-party authority recognized by the marketplace provide validated attributes. Potential authorities include Facebook, Twitter, or Google accounts (through OpenID); Verisign or PKI trust establishment regimes; companies that hold records on individuals like Equifax; or other organizations. Each authority can assign the user an attribute in the authority's namespace, and sign it with their key. They can optionally include metadata with each attribute specifying their level of confidence in the accuracy of the provided attribute. This marketplace can be hosted by a provider 102, a reseller 103, or a third party. The marketplace can be embodied via one or more computing devices, such as those described herein, programmed to perform the functions of the marketplace, and in communication with one or more of the user interface 101, the provider 102, and the reseller 103, to exchange data associated with the marketplace functions.

When a provider 102 publishes information about a data source to the marketplace they include two sets of attributes. The first attribute set is used to specify what attributes must be submitted in order for the provider to verify access to a particular data source. The provider would determine this set based on their level of trust for each authority's attributes; for example, some might find the presence of a Facebook account sufficient proof that the user is over the age of thirteen, while others would require additional evidence. The user interface 101, or the reseller 103 on their behalf, can include these required attributes in their request (via the attributes 202 of a generated query job 200 and/or the attributes 252 of a query modifier 250), and the provider compares the value of the attributes to their requirements. This requires established trust agreements among the resellers 103 and involved providers 102; a small-scale solution would be off-line informal trust agreements; at a larger scale, a framework for establishing or negotiating trust can be employed. A provider 102 can register as an authority and require attributes only they can assign, which would allow them to control the mechanisms for authorizing users more completely. The second attribute set is used to specify what attributes a user must have in order to view metadata about a particular data source. The marketplace is responsible for enforcing this limit.

User interfaces 101 are informed of the attributes required, and the resellers 103 involved in the chain, for any data source to which they wish to submit query jobs. They have the opportunity to acquire the additional attributes from authorities if required, or to choose an alternative data source. They will not see the provider's rules. Thus, simply having the required attributes is not sufficient to run a query job. For example, one attribute might be 'age' as verified by a credit card company; a user interface sends this signed attribute to the provider in a query job 200, and the provider 102 checks the value against its rules to assess whether the user interface 101 is authorized to run the submitted query job 200 on its data source. As discussed above with regard to FIGS. 2-4, the attributes associated with a restriction or access for a particular user (via interface 101) or reseller 103 can be propagated along the chain.

For convenience, the marketplace maintains a list of available attributes from all registered authorities. Providers can specify a given attribute (e.g. age) from a specific authority, or from any authority verifying that attribute. The marketplace also maintains quality/satisfaction ratings of each provider 102 and reseller 103, which users can use to identify which resellers and providers they might be willing to send their attributes through. It may hide certain data sources from users based on its own rules (e.g. depending on what package the user purchased) or on constraints expressed by the provider. The marketplace may provide a web interface with which data analysts interact with data providers and authorities; it may also build on existing work in the services community regarding automated service discovery.

The following is an illustrative use case of an implementation of the systems and methods of the inventive subject matter to the MapReduce technology.

The inventive subject matter allows data analysts to run MapReduce (MR) jobs on some portion of a data provider's Big Data, while affording the data provider 102 total, fine-grained control over access to each piece of data, and allowing run-time transformation of the data. This run-time mediation is provided by prefixing the user's MapReduce job with an additional Modifying Map step (resulting in a MapMapReduce, or "MMR", job) where the provider can implement access control, data segmentation, and/or data transformation. The run-time transformation of the Modifying Map serves to modify or restrict access to data before the consumer or end-user can access it. The Modifying Map ("MM") can also control Map tasks at a low-level, including measuring or limiting execution time, and perform other functions such as those described with regard to the query modifiers above.

In this implementation, resellers add their own Modifying Maps between the provider's Modifying Map and the user's Map. Because the data provider is the sole arbiter of which data is passed to the reseller, and the reseller then decides which data is sent to the user, each participant retains the control they need. Each map( ) invocation may transform the data from the original key-value pair provided to the provider's map method.

The provider packages the submitted code as a JAR file with their Modifying Map and other supporting code, and executes the MMR job. They respond to requests for progress by querying the Hadoop JobTracker and returning a response. They respond to requests for results by verifying successful job completion, then streaming the results from HDFS.

A reseller offers the same API as all the providers, allowing users to move among resellers and providers freely. Incoming compiled Map code is augmented with the reseller's Modifying Map, then passed to the next reseller in the chain (or the provider) via their API. Requests for status updates or results are similarly passed on, and the result returned to the requestor.

Figure 5:
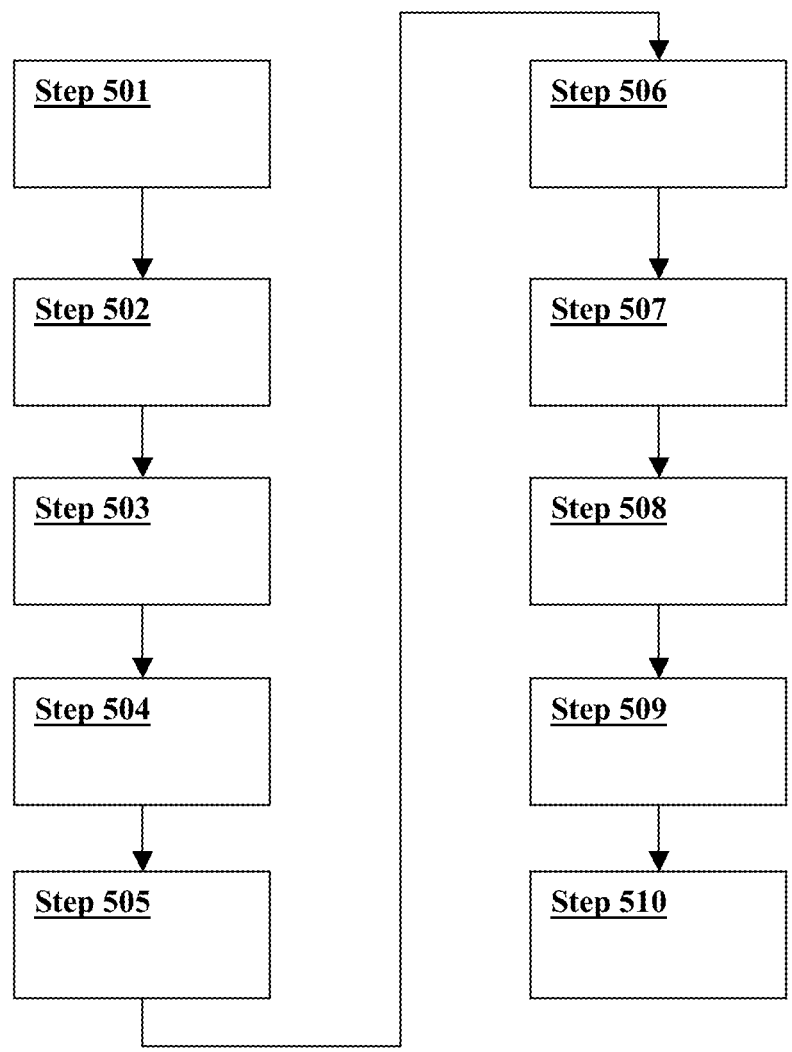
FIG. 5 provides a flowchart of the provider-side runtime functions executed in an environment implementing MapReduce technology, according to embodiments of the inventive subject matter.

FIG. 5 provides a flowchart overview of the provider functions responsive to receiving a MapReduce job, in this case from a multiple-reseller environment such as the one illustrated in FIG. 3.

At step 501, the MapReduce job from the last reseller (e.g., the requestor) in the chain is received by the provider. In this example, the MapReduce job includes the map( ) step and reduce( ) step as submitted by the user, the modifying map added by the first reseller in the chain, and the modifying map added by the last reseller in the chain. For each link in the chain (the user, the first reseller, and the second reseller), the MapReduce job also includes corresponding attributes.

At step 502, the provider identifies a data source based on attributes associated with the requestor, and invokes a Modifying Map associated with the data source. In embodiments, the identification of a data source can be performed by identifying a Modifying Map based on one or more of the attributes of the requestor, thereby being a de-facto identification of a data source. The identification can be performed via a matching of one or more of the attributes of the requestor with attributes of the provider's Modifying Map. In embodiments, the Modifying Map can include a map( ) step, and a filter( ) step, or can include a map( ) step that includes the invocation of the filter( ) step prior to any data transformation and access permission.

At step 503, the Modifying Map is called, and the provider verifies whether the requestor is authorized to access the data source. As described above, in embodiments the map( ) step can perform this verification by invoking the filter( ) step prior to performing any transformation. The filter( ) step can verify that the requestor is authorized to access data from the data source based on requestor attributes, such as the first set of attributes described above. Attributes can include signed or 'certified' attributes as discussed above. The attributes can include role attributes, identifier attributes, analysis attributes (e.g., the processes that will be performed on the data or allowed to be performed on the data by the requestor), etc. Depending on the access desired by the requestor, the MapReduce job can also include the second set of attributes described above, such as to provide access to metadata or another "tier" of data access.

At step 504, the map( ) step is carried out if the requestor is verified, and the execution of the map( ) step generates a Modifying Map output according to the transformations and other functions associated with the map( ) step. In embodiments, the filter( ) step can work on a data element level within a data source, as described above. In other embodiments, the filter( ) can act as a general verification for a data source as a whole. In these embodiments, the result of the filter( ) operation can be to allow access to the data source as a whole or deny access to the entirety of the data source.

At step 505, the provider moves on to the Modifying Map of the requestor. As with the prior Modifying Map, the provider first verifies that the first reseller is allowed to access the data source based on the attributes of the first reseller. This can, as was done with the MM for the retailer, be performed via the filter( ) step of the MM of the requestor.

At step 506, the map( ) step of the requestor is executed, and the transformation associated with this map( ) step are performed, generating a Modifying Map output for the requestor.

Steps 505 and 506 can be performed using the Modifying Map output of the provider as the input to the requestor's Modifying Map, such that the filter( ) and map( ) steps are only being implemented for data that has already been access-controlled or otherwise transformed.

Steps 508 and 509 mirror steps 505 and 506, respectively, as executed according to the first reseller's Modifying Map. As such, the user is verified based on the user's attributes and the first reseller's map( ) step is then invoked upon verification. As with the requestor, the first reseller's Modifying Map can use the output from the requestor's Modifying Map as its input.

If any additional resellers were involved in the system, the processes of steps 505 and 506 would be repeated for each additional reseller, until the last reseller is reached at steps 508 and 509.

At step 510, the user's MapReduce job is carried out based on the data as transformed by the combination of the provider's Modifying Map, the requestor's (e.g., last reseller) Modifying Map and the first reseller's Modifying Map. Once the user's MapReduce job is carried out, the results can be provided for presentation to the user via the user interface 101.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. At least one non-transitory computer-readable storage medium storing instructions that, when executed by at least one processor, cause the at least one processor to:
   receive, from a requestor, a requestor query job comprising:
   a requestor query step comprising a requestor map step and a requestor reduce step; and
   a set of requestor data values wherein the set of requestor data values defines access permission credentials with respect to one or more data sources;
   identify a data source based on the set of requestor data values;
   prefix the requestor query job with a query modifier associated with the identified data source, the query modifier comprising:
   a filter; and
   a data source query modifier step comprising a data source map step and a data source reduce step;

verify that the requestor is authorized to access data elements from the data source based on the filter and set of requestor data values;

execute, in response to verifying the requestor, the data source map step and the data source reduce step on the data elements from the data source to produce a requestor modifier output wherein the requestor modifier output comprises a subset of the one or more data sources; and execute the requestor map step and the requestor reduce step using the requestor modifier output to produce a requestor output.

2. The at least one non-transitory computer-readable storage medium of claim 1, further comprising instructions that cause the at least one processor to:

generate a result view based on the requestor output; and provide the result view to the requestor.

3. The at least one non-transitory computer-readable storage medium of claim 1, wherein:

the requestor query step in the requestor query job comprises a requestor query modifier step, the requestor query job further comprising:

a requestor filter; and a second requestor query job corresponding to a second requestor, the second requestor query job comprising:

a second requestor query step corresponding to the second requestor;

a second set of requestor data values corresponding to the second requestor; and the instructions further cause the at least one processor to:

verify, after producing the requestor output, that the second requestor is authorized to access the data from the data source according to the requestor output based on the requestor filter and the second set of requestor data values;

execute the second requestor query step to produce a second requestor output;

generate a result view based on the second requestor output; and provide the result view to the second requestor.

4. The at least one non-transitory computer-readable storage medium of claim 3, wherein the first requestor comprises a reseller and wherein the second requestor comprises a requesting user interface that submitted the second requestor query job.

5. The at least one non-transitory computer-readable storage medium of claim 3, wherein the data source comprises at least one of a medical data source, a retailer data source, a financial data source, a gaming data source, a government data source, and an educational data source.

6. The at least one non-transitory computer-readable storage medium of claim 1, wherein the requestor data values includes a certified data values, and wherein the verify instruction comprises verifying that the requestor is authorized to access data elements from the data source based on the certified data values and the filter.

7. The at least one non-transitory computer-readable storage medium of claim 1, wherein the filter comprises a set of access data values for the data source, and the verify instruction further comprises matching at least a subset of the set requestor data values with at least a subset of access data values for the data source.

8. The at least one non-transitory computer-readable storage medium of claim 7, wherein:

the filter comprises a set of metadata data values for the data source;

the verify instruction further comprises matching at least a subset of the set of the requestor data values with at least a subset of the metadata data values for the data source; and wherein the instructions further cause the at least one processor to, in response to verification, allow access to metadata for the data source.

9. The at least one non-transitory computer-readable storage medium of claim 1, wherein the requestor query step comprises a database query.

10. The at least one non-transitory computer-readable storage medium of claim 1, wherein:

the requestor query step comprises a requestor data access step and at least one of a requestor data segmentation step and a requestor data transformation step; and the data source query modifier step comprises a data source data access step, and at least one of a data source data segmentation step and a data source data transformation step.

11. The at least one non-transitory computer-readable storage medium of claim 10, wherein at least one of the requestor query step the data source query modifier step further comprises a runtime limitation step, the runtime limitation step comprising at least one of a runtime duration limitation and a processor load limitation.

12. The at least one non-transitory computer-readable storage medium of claim 1, wherein the requestor query job comprises compiled code.

13. At least one non-transitory computer-readable storage medium storing instructions that, when executed by at least one processor, cause the at least one processor to:

receive, from a requestor, a requestor query job comprising: a requestor query step; and a set of requestor data values defining access permission credentials;

identify a data source based on the set of requestor data values;

prefix the query job with a query modifier associated with the identified data source, the query modifier comprising: a filter; and a data source query modifier step;

verify that the requestor is authorized to access data elements from the data source based on the filter and set of requestor data values;

execute, in response to verifying the requestor, the data source query modifier step of the query modifier on the data elements from the data source to produce a modifier output; and execute the requestor query step using the modifier output to produce a requestor output;

wherein the requestor query job comprises a requestor MapReduce job and the requestor query step comprises a requestor map step, the requestor MapReduce job further comprising a reduce step;

wherein the query modifier comprises a modifying map and the data source query modifier step comprises a data source map step; and wherein the instructions cause the at least one processor to:

execute, in response to verifying the requestor, the map step of the modifying map on the data elements from the data source to produce the modifier output as a modifying map output wherein the modifying map output comprises a subset of the data source;

execute the requestor map step using the modifying map output to produce the requestor output as a requestor map output;

execute the reduce step based on the requestor map output; and return the results of the reduce step to the requestor.

14. The at least one non-transitory computer-readable storage medium of claim 13, wherein:

the requestor map step in the requestor MapReduce job comprises a requestor modifying map step, the requestor MapReduce job further comprising:

a requestor filter step;

a second requestor map step corresponding to the second requestor;

a second set of requestor data values corresponding to a second requestor; and wherein the instructions further cause the at least one processor to:

verify, after producing the requestor map output, that the second requestor is authorized to access the data from the data source according to the requestor map output based on the requestor filter step and the second set of requestor;

execute the second requestor map step to produce a second requestor map output;

execute the reduce step based on the second requestor map output; and return the results of the reduce step to the second requestor.

* * * * *